United States Patent
Tsujii

Patent Number: 6,141,399
Date of Patent: Oct. 31, 2000

[54] IMAGE PROCESSING METHOD, IMAGE PROCESSING DEVICE, AND IMAGE PROCESSING SYSTEM

[75] Inventor: Osamu Tsujii, Utsunomiya, Japan

[73] Assignee: Canon Kabushiki Kaisha, Tokyo, Japan

[21] Appl. No.: 09/115,374

[22] Filed: Jul. 14, 1998

[30] Foreign Application Priority Data

Jul. 18, 1997 [JP] Japan ................................. 9-194513

[51] Int. Cl.[7] .................................................. G01N 23/083
[52] U.S. Cl. ........................................ 378/98.7; 378/62
[58] Field of Search .............................. 378/62, 98, 98.7; 382/131, 132

[56] References Cited

U.S. PATENT DOCUMENTS 5,493,622   2/1996   Tsuchino et al. ...................... 382/132

*Primary Examiner*—David V. Bruce
*Attorney, Agent, or Firm*—Morgan & Finnegan, LLP

[57] ABSTRACT

An image processing device for obtaining a stable image of a high quality is provided. A dynamic range compression circuit executes a dynamic range compressing process for adding a value depending on a peripheral average pixel value to a pixel value of an input image. A contrast enhancement circuit executes a contrast enhancing process to a compressed image derived by the dynamic range compression circuit. Thus, a decrease in contrast of the whole image due to an excessive increase or decrease in density of the portion where the dynamic range compressing process was executed can be prevented.

16 Claims, 4 Drawing Sheets

IMAGE PROCESSING METHOD, IMAGE PROCESSING DEVICE, AND IMAGE PROCESSING SYSTEM

BACKGROUND OF THE INVENTION

1. Field of the Invention

The invention relates to an image processing method, an image processing device, and an image processing system and, more particularly, to an image processing method, an image processing device, and an image processing system having a dynamic range compression processing function which are suitable for use in an image process, an image collection, or the like of an x-ray chest image.

2. Related Background Art

For example, since an x-ray chest image is constructed by an image of a lung sac where an x-ray can easily transmit and an image of a mediastinum where it is very difficult for the x-ray to transmit, a range where pixel values exist is very wide.

Therefore, it has been considered that it is difficult to obtain an x-ray chest image in which both of the lung sac and the mediastinum can be simultaneously observed.

To diagnose the chest by a doctor, therefore, there is a case where an x-ray image (film) for diagnosis of the lung sac and an x-ray image (film) for diagnosis of the mediastinum are individually photographed and prepared.

As a method of avoiding such a problem, therefore, there is a method called a "self compensation digital filter".

The self compensation digital filter is expressed by the following equations (1) and (2).

$$S_D = S_{org} + f(S_{US}) \quad (1)$$

$$S_{US} = \Sigma S_{org}/M^2 \quad (2)$$

where, $S_D$:pixel value after the compensation (after the process)

$S_{org}$:original pixel value (input pixel value)

$S_{US}$:average pixel value when a moving average is obtained from the original image (input image) with respect to a mask size of (M×M) pixels f(x):function having characteristics as shown in FIGS. 1A and 1B The characteristics which the function f(x) has will now be described. First, the characteristics shown in FIG. 1A are as follows. That is, now assuming that x is a signal value and $BASE_a$ is a threshold value, f(x) is equal to "0" when "x>$BASE_a$". When "0≦x≦$BASE_a$", f(x) monotonously decreases while setting a slice to the "threshold value $BASE_a$" and an inclination to "$SLOPE_a$". (Hereinafter, the function f(x) having the above characteristics is shown by "$f_a(x)$".)

Therefore, when the above equation (1) is executed on the assumption that the original pixel value $S_{org}$ is set to a density correspondence amount, an effect for an image such that a density is enhanced at a position where the average density of the image is low, is derived.

On the other hand, the characteristics shown in FIG. 1B are as follows. That is, now assuming that the signal value is labelled to x and a threshold value is set to $BASE_b$, f(x) is equal to "0" when "0≦x<$BASE_b$". When "x ≧$BASE_b$", f(x) monotonously decreases to a negative region while setting the slice to the "threshold value $BASE_b$" and an inclination to "$SLOPE_b$". (Hereinafter, the function f(x) having the above characteristics is shown by "$f_b(x)$".)

Therefore, when the above equation (1) is executed on the assumption that the original pixel value $S_{org}$ is set to the density correspondence amount, an effect for an image such that a density is reduced at a position where the average density of the image is high is derived.

By using the method by the "self compensation digital filter" as mentioned above to, for example, the mediastinum image where it is very difficult for the x-ray to transmit, a density of the mediastinum region of the x-ray chest image increases in accordance with the characteristics shown in FIG. 1A, so that the x-ray chest image by which both of the lung sac and the mediastinum can be observed can be obtained.

Besides the method by the foregoing self compensation digital filter, there is also a method of compressing a dynamic range due to a difference of characteristic amounts of anatomical regions by using a result of an anatomical segmentation.

That is, according to the above method (hereinafter, referred to as a method by the dynamic range compression), as disclosed in detail in ("Anatomic Region Based Dynamic Range Compression for Chest Radiographs Using Warping Transformation of Correlated Distribution", SPIE Medical Imaging 97), in an x-ray chest image, a mediastinum region is defined by executing a predetermined image process from a result obtained by classifying and extracting (hereinafter, referred to as "segmentation") the lung sac region, an affine transforming function for transforming a pixel value is automatically determined for the lung sac region and/or the mediastinum region, and distributions of the pixel values in the two image areas of the lung sac region and the mediastinum region and average values of their peripheral pixels are analyzed.

Even when the method by the dynamic range compression as mentioned above is used for, for example, the image of the mediastinum where it is very difficult for the x-ray to transmit, the density of the mediastinum region of the x-ray chest image increases. The x-ray chest image by which both of the lung sac and the mediastinum can be observed can be obtained.

However, in the case where the method by the "self compensation digital filter" or the method by the dynamic range compression as mentioned above is used for, for example, the image of the mediastinum where it is very difficult for the x-ray to transmit, although the density of the mediastinum region increases in the x-ray chest image and the anatomical line can be easily seen, there is a problem such that if the density of the mediastinum region is excessively raised, the contrast of the whole image including the lung sac region deteriorates.

When such an x-ray chest image is observed, an impression as if the images were overlapped is given and it is very hard for the doctor or the like to see and diagnose.

When the dynamic range compression is executed, further, since a step of deciding parameters which are necessary for such compression is not clear, a stable x-ray chest image cannot be derived.

SUMMARY OF THE INVENTION

The invention is made to eliminate the foregoing drawbacks and it is, therefore, an object to provide an image processing method which can obtain a stable image with a high quality.

Another object of the invention is to provide an image processing device and an image processing system which can obtain a stable image with a high quality.

Under such objects, according to the invention, there is provided an image processing method of adjusting gradations of an image, in which first process for correcting an image signal in such a direction as to reduce a dynamic range of the image as a whole and a second process for correcting the image signal in such a direction as to increase the dynamic range of the image as a whole are combined, correcting characteristics of the first process and correcting characteristics of the second process are different from each other, and thereby a contrast of an image of a predetermined portion is enhanced.

The correcting characteristics of one of the first and second processes are determined in accordance with a partial feature of the image.

The correcting characteristics of the other one of the first and second processes are determined irrespective of the partial feature of the image.

The second process is performed to the image which was subjected to the first process.

In the first process, the correction is performed to only the image signal corresponding to the portion where the level of the image signal lies within a predetermined level range.

In the first process, the level of pixels to be corrected is corrected in accordance with values of a plurality of pixels including peripheral pixels and, in the second process, the level of the image signal is corrected in accordance with values of the pixels to be corrected.

According to a preferred embodiment of the invention, there is provided an image processing method of executing predetermined image processes including a dynamic range compressing process, comprising the steps of: executing the dynamic range compressing process which is expressed by the following arithmetic operating equations $$S_d = S_{org} + f(S_{US}); \quad S_{US} < BASE = S_{org}; \quad S_{US} \geq BASE$$

$$S_{US} = \Sigma S_{org}/(M \times M)$$

where, $S_d$: dynamic range compression pixel value $S_{org}$: pixel value of the input image $S_{US}$: average pixel value when a moving average is obtained from the input image with respect to a mask size of (M×M pixels)

f( ): function to control a processing effect BASE: threshold value to limit a processing range; and subsequently, executing a contrast enhancing process which is expressed by the following arithmetic operating equation $$S_c = S_d + \text{expand\_coeff} \times g(S_d - BASE); \quad S_d < BASE = S_d; \quad S_d \geq BASE$$

where, $S_c$: contrast enhancement image $S_d$: dynamic range compression pixel value expand_coeff: coefficient to control a ratio of contrast enhancement BASE: threshold value g( ): function to control a processing effect.

The function f( ) is characterized by having characteristics such that f(x)=0 when "x>BASE" and f(x) monotonously decreases when "0≦x≦BASE".

The function f( ) is characterized by having characteristics such that f(x)=0 when "0<x<BASE" and f(x) monotonously decreases to a negative area when "x≧BASE".

The threshold value BASE is a value determined on the basis of an anatomical segmentation of the image.

Either one or both of the function f( ) and the function g( ) are non-linear functions.

The invention relates to an image processing method of an x-ray image.

According to a preferred embodiment of the invention, there is provided an image processing device for executing predetermined image processes including a dynamic range compressing process, comprising: dynamic range compressing means for executing the dynamic range compressing process which is expressed by the following arithmetic operating equations $$S_d = S_{org} + f(S_{US}); \quad S_{US} < BASE = S_{org}; \quad S_{US} \geq BASE$$

$$S_{US} = \Sigma S_{org}/(M \times M)$$

where, $S_d$: dynamic range compression pixel value $S_{org}$: pixel value of the input image $S_{US}$: average pixel value when a moving average is obtained from the input image with respect to a mask size of (M×M pixels)

f( ): function to control a processing effect

BASE: threshold value to limit a processing range; and contrast enhancing means for executing a contrast enhancing process which is expressed by the following arithmetic operating equation $$S_c = S_d + \text{expand\_coeff} \times g(S_d - BASE); \quad S_d < BASE = S_d; \quad S_d \geq BASE$$

where, $S_c$: contrast enhancement image $S_d$: pixel value of a compression image obtained by said dynamic range compressing means expand_coeff: coefficient to control a ratio of contrast enhancement BASE: threshold value g( ): function to control a processing effect to the compression image obtained by the dynamic range compressing means The above and other objects and features of the present invention will become apparent from the following detailed description and the appended claims with reference to the accompanying drawings.

DETAILED DESCRIPTION OF THE PREFERRED EMBODIMENT

An embodiment of the invention will now be described hereinbelow with reference to the drawings.

First, an image processing method according to the invention is applied to an image processing method of an x-ray chest image including, for example, an image of a lung sac where an x-ray can easily transmit (lung sac region) and an image (mediastinum region) of a mediastinum where it is very difficult for the x-ray to transmit.

According to the image processing method, an anatomical segmentation of the x-ray chest image is first performed and an image of a lung sac is extracted.

Specifically speaking, for example, as disclosed in ("Automatic Segmentation of Anatomic Regions in Chest Radiographs using an Adaptive-Sized Hybrid Neural Network", SPIE Medical Imaging 97), density information which each pixel has, anatomical address information, and entropy information around the pixel are used as features and are learned by a neutral network and the segmentation is executed.

In more detail, whether a target region is the lung sac or another region is discriminated every pixel by using the density information which each pixel has, the anatomical address information, and an entropy around the pixel. As discriminating means, a result obtained by learning with a few images is applied to the other image by using a neutral network.

The most important information in this method is the anatomical address information which is allocated to each pixel and it largely exerts an influence on the performance of the method. Specifically speaking, as for the anatomical address information, the profiles in the horizontal direction and vertical direction of the image are used, a peak is searched while getting their primary differentiations or the like, points where the right and left lungs and the collarbone cross are detected, and the diaphragm gland of the right lung is detected. By using those extraction points as references, the anatomical address information is allocated to each pixel.

Figure 2:
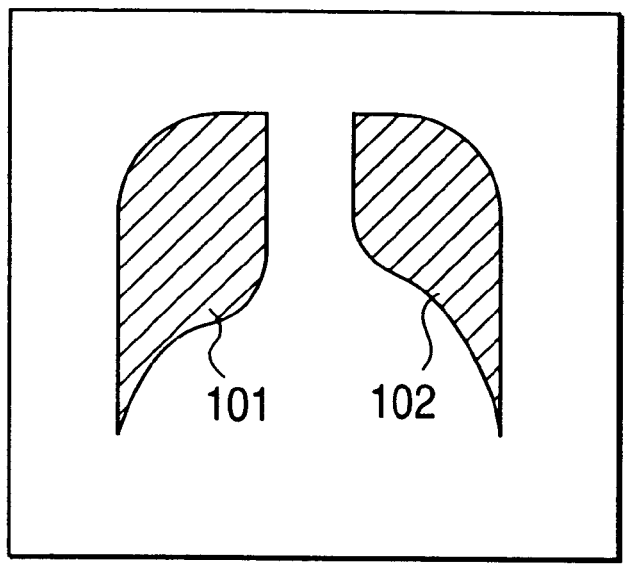
FIG. 2 is a diagram for explaining a result of a segmentation of a lung sac image which is used in an embodiment of an image processing method according to the invention.

Thus, lung sac regions 101 and 102 are extracted as shown in FIG. 2.

Figure 3:
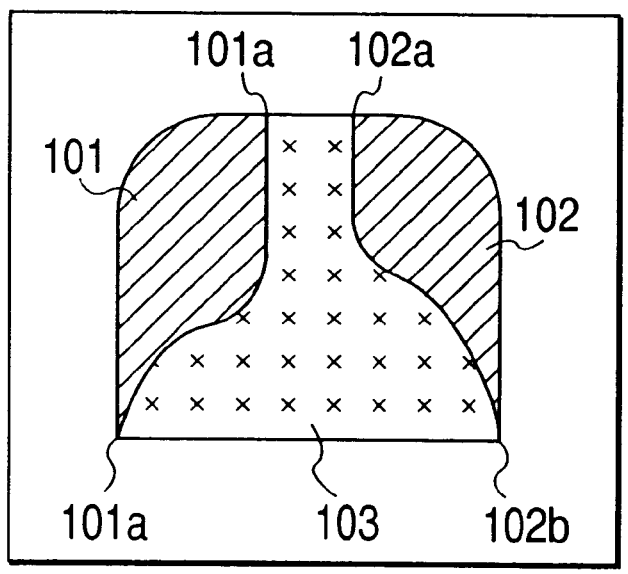
FIG. 3 is a diagram for explaining a decision of a mediastinum image according to the result of the segmentation.

As shown in FIG. 3, on the basis of extraction results (FIG. 2) of the lung sac regions 101 and 102, a closed space 103 which is formed by connecting an upper edge portion 101a of the left lung sac region 101 and an upper edge portion 102a of the right lung sac region 102 and connecting a lower edge portion 101b of the left lung sac region 101 and a lower edge portion 102b of the right lung sac region 102 is defined as an image of the mediastinum (mediastinum of a broad meaning).

Parameters which are necessary to perform the dynamic range compressing process are determined by using the result of the anatomical segmentation as mentioned above.

In the x-ray chest image, a region where it is necessary to perform the dynamic range compressing process is a mediastinum portion, a diaphragm portion, a portion where the density of a heart portion is very low, or a portion where the density of a lung sac center portion is very high.

As an example, it is now assumed that the dynamic range compressing process is executed to the mediastinum region.

Besides the mediastinum region, a dynamic range compressing process, which will be explained hereinlater, can be also similarly performed to a diaphragm portion, a portion where the density of the heart portion is very low, a portion where the density of the lung sac center portion is very high, or a lung sac portion.

When the dynamic range compressing process is executed, outline information of the image is not used but the anatomical information, for example, information of the highest density DL in the lung sac region and information of the lowest density DM in the image area in the mediastinum region are used.

The highest density DL of the lung sac and the lowest density DM of the mediastinum are obtained by using the result of the segmentation. As shown in FIGS. 2 and 3, in the whole area of the image, since the areas corresponding to the lung sac region and the mediastinum region are defined, the pixels included in those regions can be selected. That is, it is sufficient to detect the highest value and the lowest value for the pixels included in each of the lung sac region and the mediastinum region. Specifically speaking, it is sufficient to scan the image from the left upper position to the right lower position and to detect the highest value for the pixels included in the lung sac and the lowest value for the pixels included in the mediastinum. If the averaged reduction image is used as a target image, since the value of each pixel has been averaged, a variation in noises can be also suppressed to a certain extent.

Further, on the basis of the information of the highest density DL and the lowest density DM, the dynamic range compressing process using the self compensation digital filter is executed.

Figure 1A:
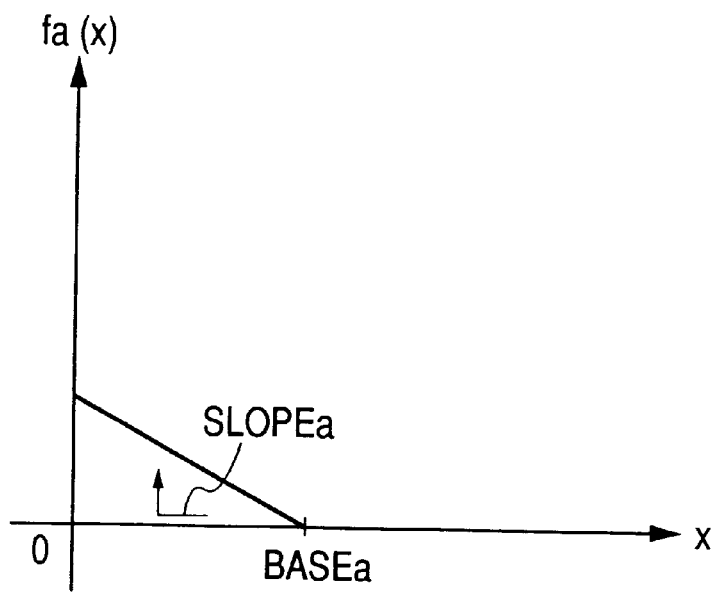
FIGS. 1A and 1B are diagrams for explaining an example of dynamic range compressing functions of a low density portion and a high density portion by a self compensation digital filter.

Necessary parameters to be determined in case of performing the dynamic range compressing process to the mediastinum region are the slice $BASE_a$ and inclination $SLOPE_a$ shown in FIG. 1A. Necessary parameters to be determined in case of performing the dynamic range compressing process to the lung sac region are the slice $BASE_b$ and inclination $SLOPE_b$ shown in FIG. 1B.

To execute the dynamic range compressing process to the mediastinum region, the slice $BASE_a$ and inclination $SLOP_a$ shown in FIG. 1A are determined.

That is, with respect to the decision of the slice $BASE_a$, a parameter compress_ratio is used.

The parameter compress_ratio controls from which position the dynamic range compressing process is started in the density interval between the highest density DL of the lung sac region and the lowest density DM of the mediastinum region. A predetermined value obtained by a clinical experience, which will be explained hereinlater, is set as such a parameter. The density controlled by such a parameter is set to the slice $BASE_a$.

Therefore, the slice $BASE_a$ is determined by the following equation (3).

$$BASE_a = DM + \text{compress\_ratio} \times (DL - DM) \tag{3}$$

With respect to the determination of the inclination $SLOPE_a$, the inclination $SLOPE_a$ is a parameter to adjust the intensity of the dynamic range compression and is set to a predetermined value obtained by a clinical experience, which will be explained hereinlater.

The dynamic range compressing process for the mediastinum region is subsequently executed on the basis of the slice $BASE_a$ and inclination $SLOPE_a$ determined as mentioned above.

From the function $f_a(x)$ shown in FIG. 1A determined by the slice $BASE_a$ and inclination $SLOPE_a$, the dynamic range compressing process is expressed by the following equations (4) and (5).

$$S_d = S_{org} + f_a(S_{US}); \; S_{US} < BASE_a = S_{org}; \; S_{US} \geq BASE_a \tag{4}$$

$$S_{US} = \Sigma S_{org}/(M \times M) \tag{5}$$

where, $S_d$: pixel value obtained by compressing the dynamic range $S_{org}$: input pixel value $S_{US}$: (unsharp signal) average pixel value when a moving average of the input image is obtained with respect to the mask size of (M×M) pixels A contrast enhancing process as one of the characteristic points of the invention will be subsequently executed.

That is, although a process to reduce the density is performed to the image area (image area of the mediastinum region) compressed by the foregoing dynamic range compressing process, a contrast enhancing process is executed in this instance.

The contrast enhancing process in this instance is expressed by the following equations (6) and (7).

$$S_c = S_d + \text{expand\_coeff} \times (S_d - \text{BASE}_a); \ S_d < \text{BASE}_a = S_d; \ S_d \geq \text{BASE}_a \quad (6)$$

$$\text{expand\_coeff} = [\{1/(1-\text{SLOPE}_a)\} - 1] \times \text{expand\_ratio} \quad (7)$$

where, $S_c$: image value of the image after completion of the contrast enhancement $S_d$: dynamic range compression pixel value obtained by the foregoing dynamic range compressing process expand_ratio: contrast enhancement ratio from the dynamic range compression pixel value $S_d$ expand_coeff: coefficient to control the contrast enhancement ratio $\text{BASE}_a$: slice mentioned above $\text{SLOPE}_a$: inclination Therefore, by executing the equations (6) and (7), the density of the mediastinum region decreases and the contrast is enhanced. That is, in the x-ray chest image, although the density of the mediastinum region does not increase, a state similar to that when the density is raised is obtained.

Consequently, it is possible to prevent the conventional problem such that in spite of a fact that the density of the mediastinum region increases and the anatomical line can be easily seen, if the density of the mediastinum region is excessively raised, the whole contrast of the chest image including the lung sac region deteriorates. When the x-ray chest image is observed, it can be observed in a very good state without giving an impression such that the images are overlapped to the observer.

In the above equation (3), when statistically considering, when the parameter compress_ratio is increased, the dynamic range compression is performed in the lung sac region and the mediastinum region so as to fairly enter the lung sac region. On the contrary, when the parameter compress_ratio is reduced, even in the mediastinum region, the dynamic range compression is not performed in only the low density portion.

Therefore, for example, in the x-ray image of the chest front surface, in the case where the parameter compress_ratio is set to compress_ratio=0.3, the clinically best experimental result was obtained.

In the case where the inclination $\text{SLOPE}_a$ mentioned above is set to $\text{SLOPE}_a = 0.325$, the clinically best experimental result was obtained.

That is, experimentally, as parameters depending on the image, there are two parameters of the highest density DL of the lung sac region and the lowest density DM of the mediastinum region. The parameter compress_ratio and inclination $\text{SLOPE}_a$ to determine the intensity and range of the dynamic range compression are regarded as values which are derived from the clinical experience.

Further, the foregoing contrast enhancement ratio expand_ratio is not the parameter depending on the image but is also a value which is obtained from the clinical experience. In the case where expand_ratio=0.8, the best experimental result was obtained.

Therefore, with respect to the parameters of "compress_ratio", "$\text{SLOPE}_a$", and "expand_ratio", the values obtained by the clinical experience are set.

Figure 4:
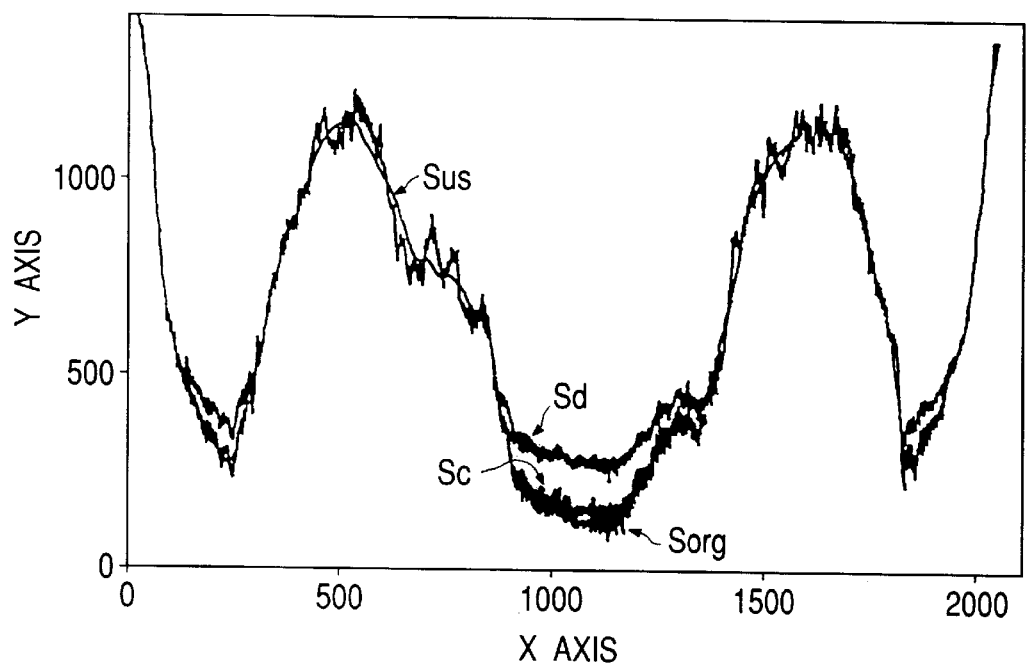
FIG. 4 is a diagram for explaining an example of a profile in the horizontal direction of center portions in chest images which were subjected to a dynamic range compressing process and a contrast enhancing process, respectively.
Figure 5:
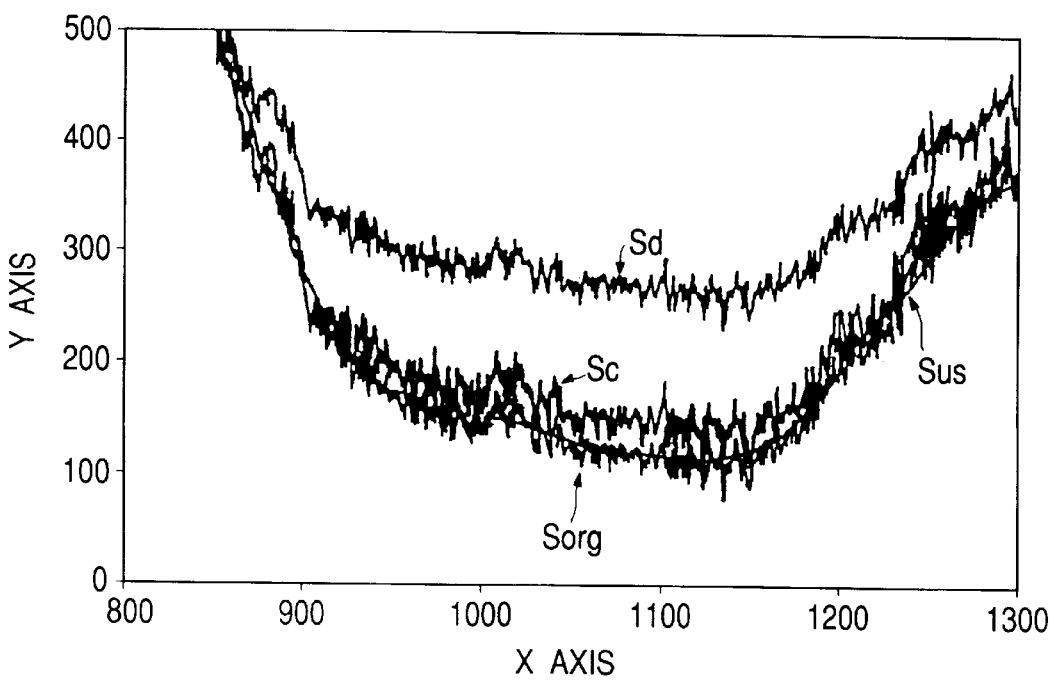
FIG. 5 is a diagram for explaining a profile obtained by enlarging a mediastinum region in the example of the profile mentioned above.

FIGS. 4 and 5 show examples of a profile (FIG. 4 mentioned above) in the horizontal direction of the center portion of the x-ray image of the chest front surface and an enlarged profile (FIG. 5 mentioned above) of the mediastinum region in the case where compress_ratio=0.3

$\text{SLOPE}_a=0.325$ expand_ratio=0.8

Figure 1B:
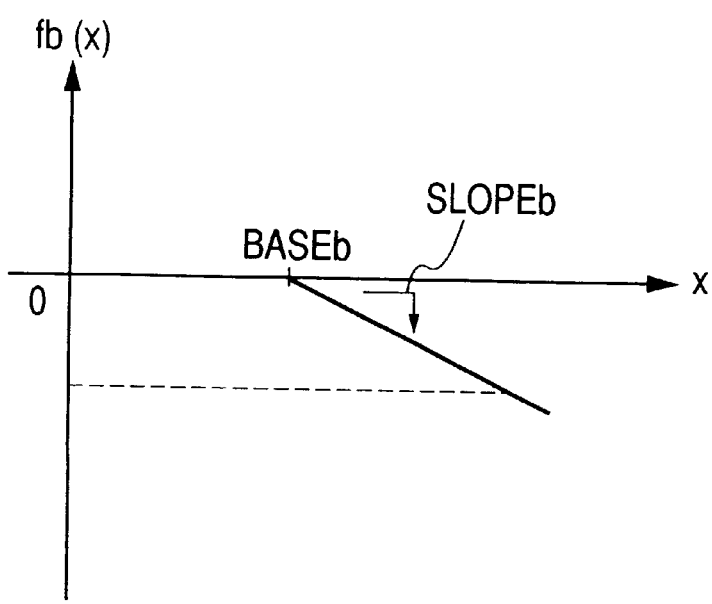

According to the above image processing method, although the dynamic range compressing process has been performed to the mediastinum region, the invention is not limited to this region but the dynamic range compressing process can be also executed to the lung sac region by using the function $f_b(x)$ shown in FIG. 1B. Or, the dynamic range compressing process can be also executed to both of the mediastinum region and the lung sac region.

When the above contrast enhancing process is expressed by the following equation (8), $$S_c = S_d + \text{expand\_coeff} \times g(S_d - \text{BASE}_a); \ S_d < \text{BASE}_a = S_d; \ S_d \geq \text{BASE}_a \quad (8)$$

in the above image processing method, a control of the contrast enhancement is performed in accordance with a linear function of $g(x)=x$ That is, the contrast enhancement control such that an effect of linearity can be derived is performed with regard to the density difference shown by $(S_d-\text{BASE}_a)$. However, by applying a function of non-linearity to $g(x)$, the contrast enhancement control can be also modified to a control such as to obtain the effect of the non-linearity as for the density difference shown by $(S_d-\text{BASE}_a)$.

Figure 6:
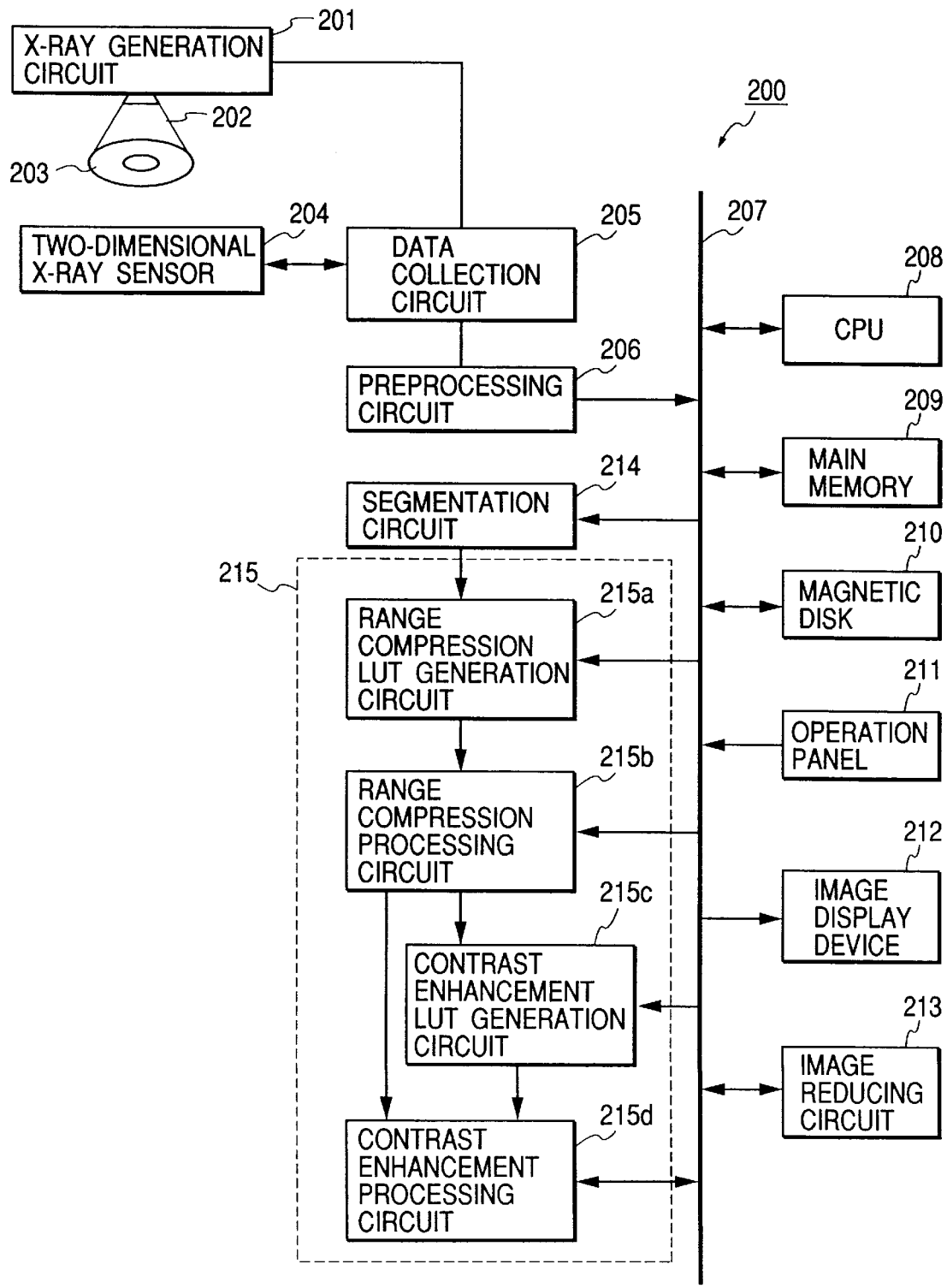
FIG. 6 is a block diagram showing a construction of an image processing device to which the foregoing image processing method is embodied.

Subsequently, an example of a device to realize the foregoing image processing method will now be described. FIG. 6 is a diagram showing an embodiment of an image processing device 200.

The image processing device 200 is an image processing device of an x-ray image having a dynamic range compressing function. As shown in FIG. 6, the image processing device 200 comprises: a preprocessing circuit 206; a segmentation processing circuit 214; a dynamic range compression circuit 215; a CPU 208; a main memory 209; a magnetic disk driver 210; an operation panel 211; an image display device 212; and an image reducing circuit 213. Those circuits can mutually transmit and receive data through a CPU bus 207.

The image processing device 200 also has: a data collection circuit 205 connected to the preprocessing circuit 206; and a two-dimensional x-ray sensor and an x-ray generation circuit 201 connected to the data collection circuit 205.

Further, the dynamic range compression circuit 215 comprises: a range compression LUT (Look Up Table) generation circuit 215a connected to the segmentation processing circuit 214; and a range compression processing circuit 215b connected to the range compression LUT generation circuit 215a; a contrast enhancement LUT generation circuit 215c;

and a contrast enhancement processing circuit 215d connected to the range compression processing circuit 215b and contrast enhancement LUT generation circuit 215c. Those circuits are also connected to the CPU bus 207.

In the image processing device 200 as mentioned above, first, various data and the like including programs which are necessary for processes in the CPU 208 are stored into the main memory 209 serving as a recording medium. The main memory 209 also includes a work memory serving as a work area for the CPU 208.

The CPU 208 executes an operation control and the like of the whole device according to the operation from the operation panel 211 by using the main memory 209.

Thus, the image processing device 200 operates as follows.

First, the x-ray generation circuit 201 emits an x-ray beam 202 to a specimen 203 to be examined in response to a timing signal from the data collection circuit 205.

The x-ray beam 202 emitted from the x-ray generation circuit 201 transmits the specimen 203 while being attenuating and reaches the 2-dimensional x-ray sensor 204 and is generated as an x-ray image by the 2-dimensional x-ray sensor 204.

It is now assumed that the x-ray image which is generated from the 2-dimensional x-ray sensor 204 is, for instance, a chest image including images of the lung sac and the mediastinum as mentioned above.

The data collection circuit 205 converts the x-ray image generated from the 2-dimensional x-ray sensor 204 into an electric signal and supplies to the preprocessing circuit 206.

The preprocessing circuit 206 executes preprocesses such as offset correcting process, gain correcting process, and the like to a signal (x-ray image signal) from the data collection circuit 205.

The x-ray image signal which was preprocessed by the preprocessing circuit 206 is transferred to the magnetic disk driver 210 and image reducing circuit 213 through the CPU bus 207 under the control of the CPU 208.

The magnetic disk driver 210 files the x-ray image signal transferred through the CPU bus 207 into the magnetic disk as raw image information.

The image reducing circuit 213 reduces the x-ray image signal transferred through the CPU bus 207 by a reduction ratio and a reducing method according to the control of the CPU 208.

The reduction ratio in the image reducing circuit 213 is set to a value such that each side of the image is reduced into ⅛ to ⅟₁₆ and is set by the operation panel 211.

As a reducing method in the image reducing circuit 213, there is an average reducing method or a subsampling (thinning-out) method. Any one of the reducing method to be used is set by the operation panel 211. For example, it is set by the operation panel 211 so as to use the averaging and compressing method with less noise.

Therefore, by the operation of the operation panel 211, the CPU 208 controls the image reducing (compressing) circuit 213 so as to execute the compression so as to reduce each side of the image into ⅛ to ⅟₁₆ by using the averaging and compressing method.

As mentioned above, by executing the reducing process in the image reducing circuit 213, a segmentation time in the segmentation processing circuit 214 can be reduced. The processes can be efficiently progressed.

The x-ray image signal (reduction image signal) which was subjected to the reducing process in the image reducing circuit 213 is transferred to the segmentation processing circuit 214 through the CPU bus 207 under the control of the CPU 208.

The segmentation processing circuit 214 defines the mediastinum region by performing the segmentation of the lung sac region as mentioned above in the reduction image signal transferred through the CPU bus 207, thereby detecting the highest density DL of the lung sac region and the lowest density DM of the mediastinum region.

The segmentation processing circuit 214 supplies the highest density DL of the lung sac region and the lowest density DM of the mediastinum region which were detected to the dynamic range compression circuit 215.

In this instance, the preprocessed image stored on the magnetic disk by the magnetic disk driver 210 is transferred to the dynamic range compression circuit 215 through the CPU bus 207 by the control of the CPU 208.

On the basis of the highest density DL and lowest density DM outputted from the segmentation processing circuit 214, the dynamic range compression circuit 215 executes the dynamic range compressing process and contrast enhancing process as mentioned above to the reduction image signal transferred through the CPU bus 207.

It is now assumed that in the reduction image signal (reduction image signal of the chest), the dynamic range compressing process and the contrast enhancing process are executed to the image of the mediastinum where it is very hard for the x-ray to transmit.

That is, in the dynamic range compression circuit 215, the range compression LUT generation circuit 215a executes the arithmetic operation of the equation (3) by using the highest density DL and the lowest density DM from the segmentation processing circuit 214 by setting, for example, compress_ratio=0.3

$SLOPE_a=0.325$, thereby determining the slice $BASE_a$.

On the basis of the decided slice $BASE_a$, the range compression LUT generation circuit 215a generates a range compression LUT having the characteristics of the function $f_a(X)$ shown in FIG. 1A and supplies to the range compression processing circuit 215b.

On the basis of the range compression LUT from the range compression LUT generation circuit 215a, the range compression processing circuit 215b executes the arithmetic operating processes of the equations (4) and (5) to the preprocessed image signal transferred through the CPU bus 207, thereby forming a dynamic range compression image signal in which the dynamic range compression has been performed to the mediastinum region and supplying to the contrast enhancement processing circuit 215d.

The arithmetic operating process in the equation (5) in the range compression processing circuit 215b is executed by an arithmetic operating circuit of hardware in a real-time manner.

At this time, the contrast enhancement LUT generation circuit 215c forms contrast enhancement LUTs which are realized by the equations (6) and (7) by the above equation (3) and supplies to the contrast enhancement processing circuit 215d by setting, for example, compress_ratio=0.3

$SLOPE_a=0.325$ expand_ratio=0.8

On the basis of the contrast enhancement LUT from the contrast enhancement LUT generation circuit 215c, the contrast enhancement processing circuit 215d executes a process to enhance the contrast of the mediastinum region to the dynamic range compression image signal from the range compression processing circuit 215b.

As mentioned above, the arithmetic operations of the above equations (6) and (7) to perform the contrast enhancing process are realized by the contrast enhancement LUT, thereby enabling the process to be executed at a high speed in the contrast enhancement processing circuit 215d.

The dynamic range compression image signal in which the contrast of the mediastinum region has been improved by the contrast enhancement processing circuit 215d is transferred to each of the image display device 212 and magnetic disk driver 210 through the CPU bus 207 under the control of the CPU 208.

The image display device 212 displays the x-ray chest image onto the screen on the basis of the dynamic range compression image signal transferred through the CPU bus 207.

The magnetic disk driver 210 files the dynamic range compression image signal transferred through the CPU bus 207 onto the magnetic disk as x-ray chest image information after completion of the image process.

Therefore, the mediastinum region of the x-ray chest image which is displayed on the screen by the image display device 212 becomes a state similar to a density raised state without increasing the density. Both of the lung sac and the mediastinum can be observed in a very good state.

The x-ray chest image in which both of the lung sac and the mediastinum can be observed in a very good state can be preserved on the magnetic disk or the like as a file.

By merely giving the parameters (compress ratio, $SLOPE_a$, expand_ratio, etc.) to control the intensity of the dynamic range compression, range, and enhancement of the contrast, the subsequent processes can be automated and executed, so that a stable x-ray chest image can be obtained.

In the image processing device 200, the reducing process of the x-ray image is executed by the image reducing circuit 213 and the reduction image derived by the image reducing circuit 213 is supplied to the segmentation processing circuit 214. However, the image (original image) which was preprocessed by the preprocessing circuit 206 can be also supplied as it is to the segmentation processing circuit 214 without providing the image reducing circuit 213.

The invention can be applied to a device comprising one equipment as shown in FIG. 6 or can be also applied to a system comprising a plurality of equipment.

According to the invention as described above, for the pixel value of the input image, the dynamic range compressing process for adding a value depending on a peripheral average pixel value is executed and, after that, the contrast enhancing process is executed, thereby enhancing the contrast while reducing the density change due to the execution of the dynamic compressing process. Thus, it is possible to prevent the reduction of the contrast of the whole image due to the excessive increase or decrease in the density of the portion where the dynamic range compressing process has been performed. By merely giving the parameters (threshold value BASE, coefficient expand_coeff, etc.) to control the intensity of the dynamic range compressing process, range, and enhancement of the enhancing process of the contrast, the subsequent processes can be automated and executed, so that a stable x-ray image can be obtained. Therefore, a stable image of a high quality can be obtained.

By using the function f( ) having the characteristics such that f(x)=0 when "x>BASE" and f(x) monotonously decreases when "0≦x≦BASE", in the portion of a low average density of the image, a state similar to the density raised state can be obtained without increasing the density.

On the other hand, by using the function f( ) having the characteristics such that f(x)=0 when "0<x<BASE" and f(x) monotonously decreases to a negative region when "x≧BASE", in the portion of a high average density of the image, a state similar to the density reduced state can be obtained without decreasing the density.

By setting either one or both of the function f( ) and the function g( ) to control the processing effect to the non-linear functions, a state of the enhancement of the contrast can be also effected to not only the linearity but also the non-linearity.

The invention can be also applied to an x-ray image including the image of the region where the x-ray can easily transmit and the image of the region where it is very difficult for the x-ray to transmit. Thus, for example, it is possible to provide an x-ray chest image in which both of the lung sac where the x-ray can easily transmit and the mediastinum where it is very hard for the x-ray to transmit can be simultaneously observed in a good state.

Many widely different embodiments of the present invention may be constructed without departing from the spirit and scope of the present invention. It should be understood that the present invention is not limited to the specific embodiments described in the specification, except as defined in the appended claims.

What is claimed is:

1. An image processing method of adjusting gradations of an image of an anatomical part, included in an image for diagnosis, by using an un-sharn signal of the image for diagnosis comprising:
    a first correction step of correcting according to the un-sharp signal, image data representing the image for diagnosis having the un-sharp signal whose value falls within a range calculated from anatomical information of the image for diagnosis, and thereby narrowing a dynamic range of the image for diagnosis; and
    a second correction step of performing correction according to a value of the image data corrected in said first correction step, and thereby enlarging the dynamic range.

2. A method according to claim 1, wherein said image for diagnosis is an image photographed by using an x-ray.

3. A method according to claim 1, wherein the anatomical information included a maximum value of a signal in the image of the anatomical part.

4. A method according to claim 1, wherein the anatomical information includes a minimum value of a signal in the image of the anatomical part.

5. A method according to claim 1, wherein said second correction step includes a step of performing a correction processing which improves contrast of an output image, when the corrected image data falls within the calculated range.

6. An image processing method of enhancing a contrast of an image, comprising:
    a first step of correcting in a manner such that in accordance with an average value of values of a plurality of pixels including pixels around a correction pixel to be corrected, a value of said correction pixel in which said average value lies within a predetermined range approaches a center of a whole dynamic range; and
    a second step of correcting so as to allow the value of said correction pixel to approach an edge of the whole dynamic range in accordance with the value of said correction pixel to be corrected.

7. An image processing method comprising:
    a dynamic range compressing step which is expressed by the following arithmetic operating equations $S_d = S_{org} + f(S_{US})$; $S_{US} < BASE = S_{org}$; $S_{US} \geq BASE$ $S_{US} = \Sigma S_{org}/(M \times M)$ where, $S_d$: pixel value whose dynamic range was compressed $S_{org}$: pixel value of an input image $S_{US}$: average pixel value when a moving average is obtained from the input image with respect to a mask size of (M×M pixels)

f( ): function to control a processing effect

BASE: threshold value to limit a processing range; and a contrast enhancement step which is executed subsequent to said dynamic range compressing step and is expressed by the following arithmetic operating equation $$S_c = S_d + \text{expand\_coeff} \times g(S_d - \text{BASE}); \ S_d < \text{BASE} = S_d; \ S_d \geq \text{BASE}$$

where, $S_c$: contrast enhancement image $S_d$: said dynamic range compression pixel value expand_coeff: coefficient to control a ratio of contrast enhancement BASE: said threshold value g( ): function to control a processing effect.

8. A method according to claim 7, wherein said function f( ) has characteristics such that f(x)=0 when "x>BASE" and f(x) monotonously decreases when "0≦x≦BASE".

9. A method according to claim 7, wherein said function f( ) has characteristics such that f(x)=0 when "0<x<BASE" and f(x) monotonously decreases to a negative region when "x≧BASE".

10. A method according to claim 7, wherein said threshold value BASE is a value determined on the basis of an anatomical segmentation of the image.

11. A method according to claim 7, wherein either one or both of said function f( ) and said function g( ) are non-linear functions.

12. An image processing apparatus for adjusting gradation of an image of an anatomical part, included in an image for diagnosis, by using an un-sharp signal of the image for diagnosis, comprising:

first correction means for correcting according to the un-sharp signal, image data representing the image for diagnosis having the un-sharp signal whose value falls within a range calculated from anatomical information of the image for diagnosis, and thereby narrowing a dynamic range of the image for diagnosis; and second correction means for performing correction according to a value of the image data corrected by said first correction means, and thereby enlarging the dynamic range.

13. A device according to claim 12, wherein said image for diagnosis is an image photographed by using an x-ray.

14. An apparatus according to claim 12, wherein the anatomical information includes a maximum value of a signal in the image of the anatomical part.

15. An apparatus according to claims 12, wherein the anatomical information includes a minimum value of a signal in the image of the anatomical part.

16. An apparatus according to claim 12, wherein said second correction means performs a correction processing which improves contrast of an output image, when the corrected image data falls within the calculated range.

* * * * *

UNITED STATES PATENT AND TRADEMARK OFFICE
CERTIFICATE OF CORRECTION

PATENT NO. : 6,141,399
DATED : October 31, 2000
INVENTOR(S) : Osamu Tsujii

Page 1 of 1

It is certified that error appears in the above-identified patent and that said Letters Patent is hereby corrected as shown below:

Column 10,
Line 37, "$f_a(X)$" should read -- $f_a(x)$ --

Column 11,
Line 26, "(compress ratio," should read -- (compress_ratio, --

Column 12, claim 1,
Line 25, "un-sharn" should read -- un-sharp --

Signed and Sealed this

Sixteenth Day of April, 2002

Attest:

JAMES E. ROGAN
Attesting Officer    Director of the United States Patent and Trademark Office